US00PP30352P3

(12) United States Plant Patent
Lynch

(10) Patent No.: US PP30,352 P3
(45) Date of Patent: Apr. 9, 2019

(54) APPLE TREE NAMED 'SEATON99'

(50) Latin Name: *Malus domestica*
Varietal Denomination: Seaton99

(71) Applicant: Fashion Foods Limited, Nelson (NZ)

(72) Inventor: William John Edmund Lynch, Richmond (NZ)

(73) Assignee: Fashion Foods Limited, Nelson (NZ)

( * ) Notice: Subject to any disclaimer, the term of this patent is extended or adjusted under 35 U.S.C. 154(b) by 0 days.

(21) Appl. No.: 14/999,876

(22) Filed: Jul. 13, 2016

(65) Prior Publication Data

US 2017/0020044 P1 Jan. 19, 2017

(30) Foreign Application Priority Data

Jul. 15, 2015 (NZ) ..... PBR APP232

(51) Int. Cl.
*A01H 5/08* (2018.01)

(52) U.S. Cl.
USPC ..... Plt./162
CPC ..... *A01H 5/08* (2013.01)

(58) Field of Classification Search
USPC ..... Plt./161, 162
CPC ..... A01H 5/0875
See application file for complete search history.

*Primary Examiner* — Kent L Bell
(74) *Attorney, Agent, or Firm* — Leydig, Voit & Mayer, Ltd.

(57) ABSTRACT

A new and distinct variety of *Malus domestica* named 'Seaton99' characterized by a bright pink colour with faint underline stripe fully filling in to block colour; more intensively visually apparent bright pink tones than any comparable early maturing apple varieties; foreground colour over 75% of fruit surface; mild cheddar background colour; random 'flecking' exhibited to varying modest degrees in approximately 30% of fruits; early maturation; distinctive strong flavours and after-tastes; consistent and stable repeat cropping returning identical characteristics over an extended trial period; and retention and enhancement of bright colouration in long storage events.

7 Drawing Sheets

Genus and species plant claimed: *Malus domestica.*
Variety denomination: 'Seaton99'.

CROSS REFERENCE TO RELATED APPLICATION

This application claims the benefit of New Zealand Plant Variety Right Application No. APP232, filed Jul. 15, 2015, the disclosure of which is incorporated by reference in its entirety.

BACKGROUND OF THE INVENTION

The present invention relates to a new and distinct variety of apple tree hereinafter referred to as 'Seaton99'.

The discovery was made in 1999 amongst a block of 'Heritage Gala' apple trees growing in a cultivated orchard in the Tasman District of Nelson Province in New Zealand, whereby one tree on the end of a row of trees was identified that exhibited many and varied apparent mutations of the variety that was systematically planted in an orchard block of apple trees. The parent tree is believed to be a 'Heritage Gala' tree, where 'Heritage Gala' refers to a historical New Zealand bred apple variety. Due to the location of the tree and its significant different attributes from all others, it was not possible to establish whether the tree was a seedling positioned strategically for expedient observation, or a chance mutation coincidentally occurring on the end of a row of trees, as the orchard was purchased with the trees established and enquiries failed to reveal any knowledge or information.

The inventor selected and propagated trees from the identified discovery to test and consider the attributes of the discovery, and after many years of observation, trials and elimination chose two principal new apple varieties that were distinctly different visually and in eating attributes.

'Seaton99' is one of the chosen selections and was propagated from the selected plant material and planted out on rootstocks M.793, M9, and CG202 in moderate numbers to further test and examine stability and identified characteristics.

BRIEF DESCRIPTION OF THE INVENTION

Over a 15 year trial period, the inventor has established the following characteristics and differences that demonstrate 'Seaton99' as a new and distinct apple variety: 1) Bright pink with faint underline stripe fully filling in to block colour; 2) More intensively visually apparent bright pink tones than any comparable early maturing apple varieties; 3) Foreground colour over 75% of fruit surface; 4) Mild cheddar background colour; 5) Random 'flecking' exhibited to varying modest degrees in approximately 30% of fruits; 6) Early maturation affording harvest 7 to 10 days in advance of regular 'Gala' and 'Royal Gala' varieties; 7) Distinctive strong flavours and after-tastes more intense than 'Royal Gala' and its mutations, and reminiscent of historical 'Heritage Gala'; 8) Consistent and stable repeat cropping returning identical characteristics over an extended trial period; and 9) Retention and enhancement of bright colouration in long storage events, compared to fading and browning observed in regular 'Royal Gala' and 'Gala' strains when stored for extended periods.

Provided below are comparisons of the present variety to possible parental or other early maturing varieties.

TABLE 1

| Characteristic | New Variety 'Seaton99' | Comparison variety |
|---|---|---|
| Hue over colour of mature fruit | bright pink with orange hint | 'Heritage Gala' orange/red<br>'Royal Gala' - orange/red |
| Background colour at optimum harvest | mild cheddar | Lemon |
| Relative area of over-colour | 75%-95% | 'Heritage Gala' 25%-50%<br>'Royal Gala' 66%-80% |
| Relative area of back-ground colour | 5%-25% | 'Heritage Gala' 50%-75%<br>'Royal Gala' 25%-50% |
| Relative area of random flecking | 0%-2.5% | 'Heritage Gala' 0%<br>'Royal Gala' 0% |
| Relative frequency of flecking (per 100 fruits) | 33.33% | 'Heritage Gala' 0%<br>'Royal Gala' 0% |
| Relative eating attributes | stronger flavour and after-tastes | 'Royal Gala' noticeably lesser than traditional 'Gala' & 'Royal Gala' |

BRIEF DESCRIPTION OF THE DRAWINGS

The accompanying photographs illustrate the overall appearance of the new *malus* 'Seaton99' showing the colours as true as is reasonably possible with coloured reproductions of this type using a 44 mp camera.

DETAILED DESCRIPTION

Figure 1:
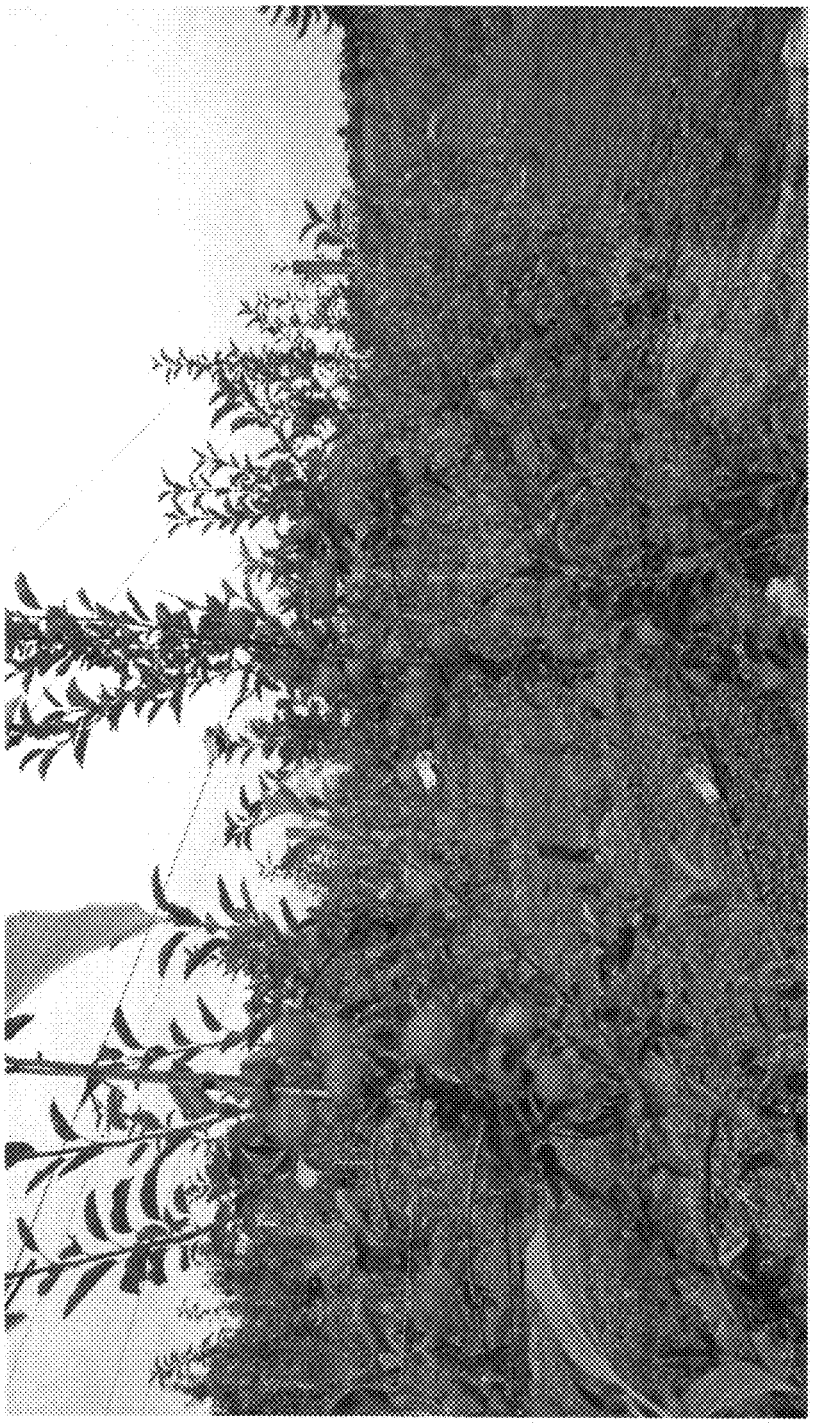
FIG. 1 shows a perspective view of cropping 'Seaton99' trees with fruit immediately prior to harvest
Figure 2:
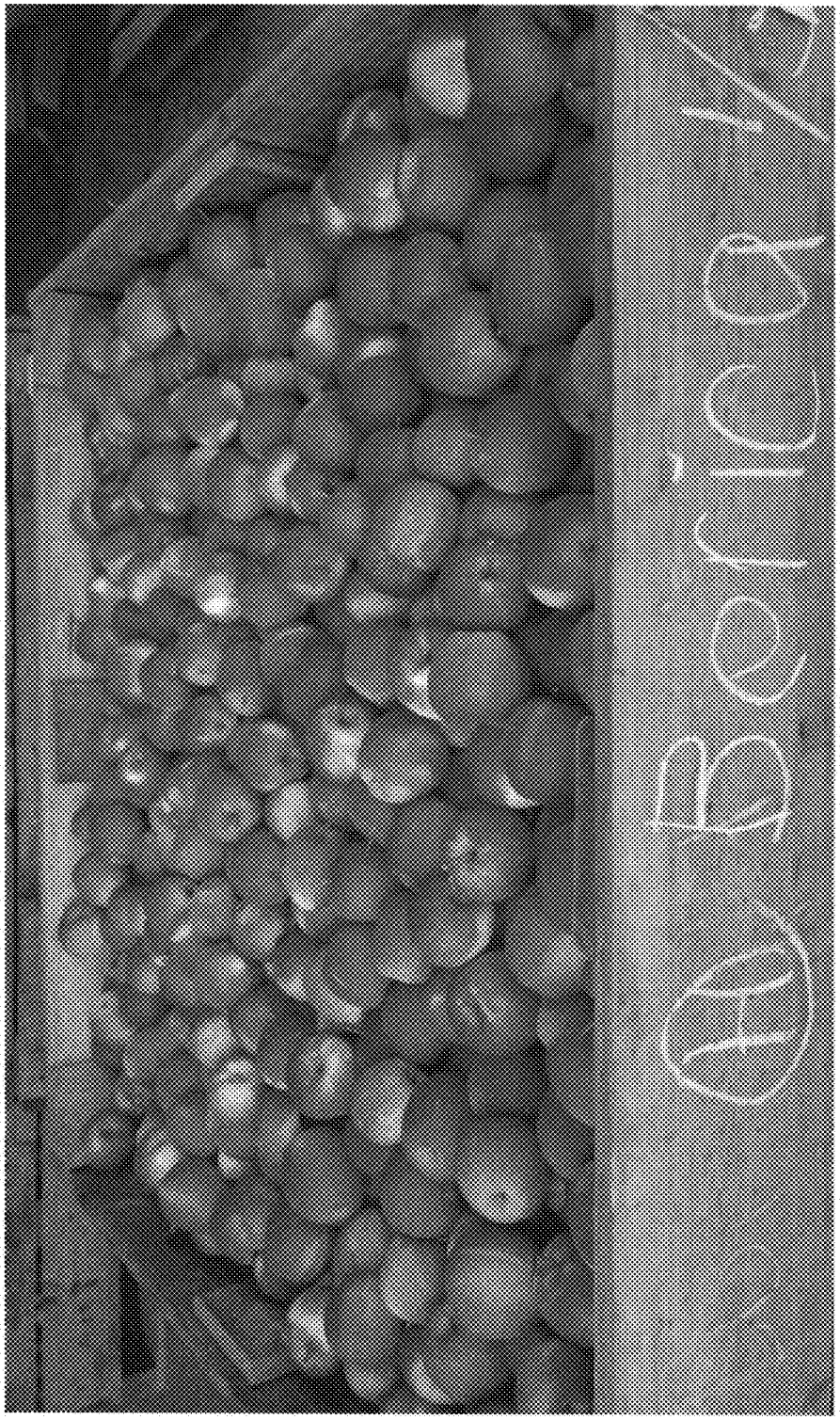
FIG. 2 shows a perspective view of the harvested 'Seaton99' fruit.
Figure 3:
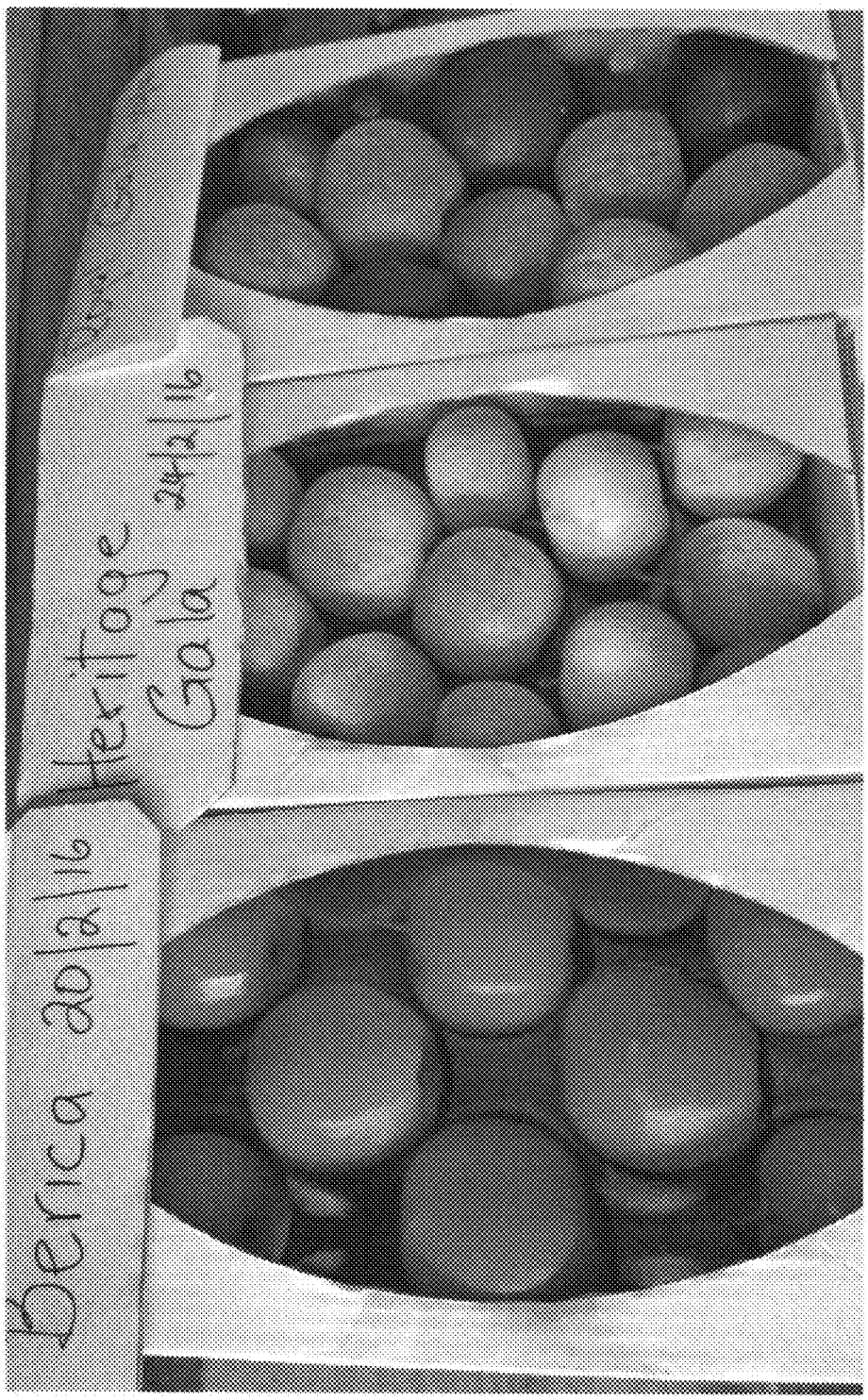
FIG. 3 shows a perspective comparison of harvested 'Seaton99' fruit alongside 'Heritage Gala' and 'Royal Gala' exhibiting distinctive visual differences
Figure 4:
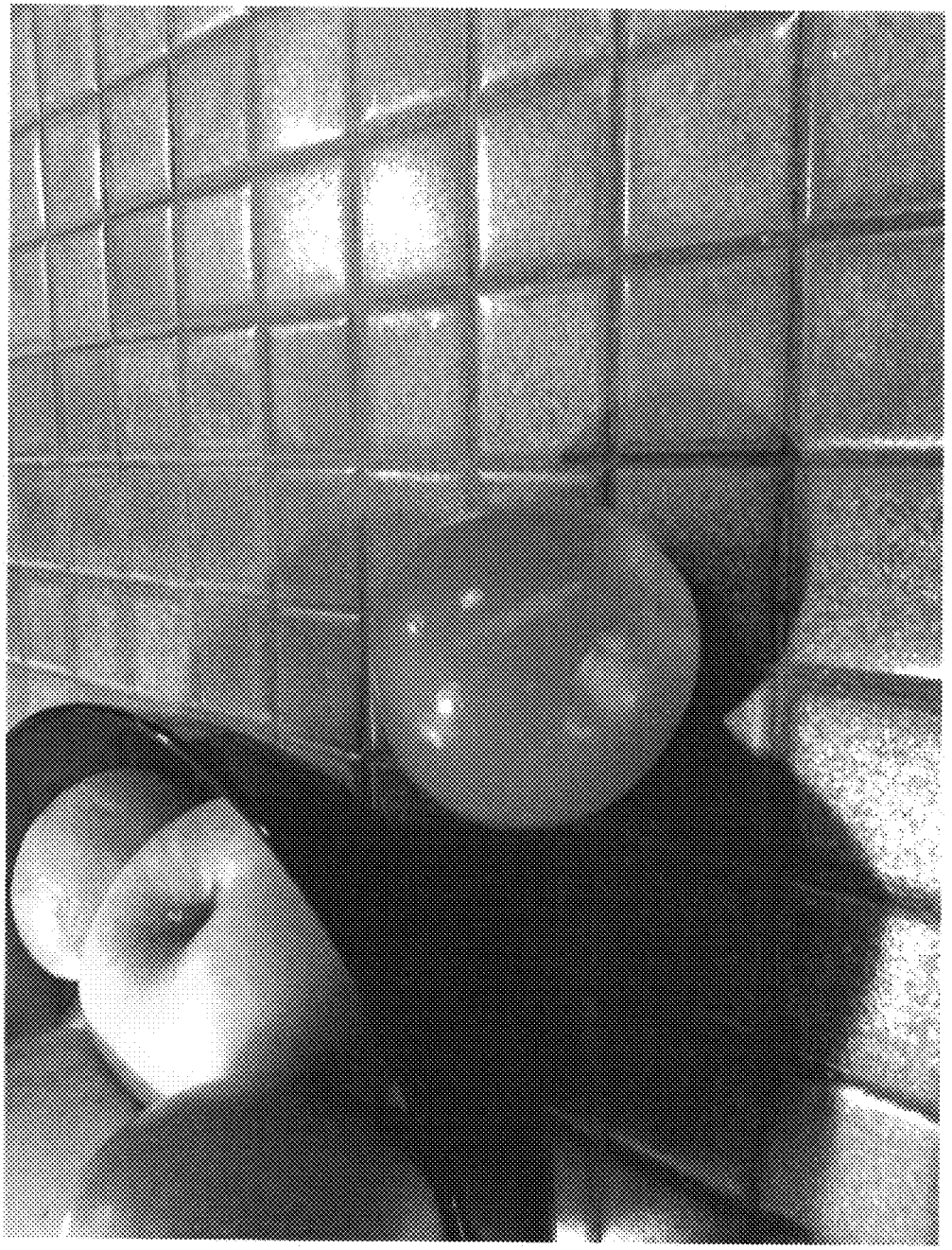
FIG. 4 shows 'Seaton99' random "flecking".
Figure 5:
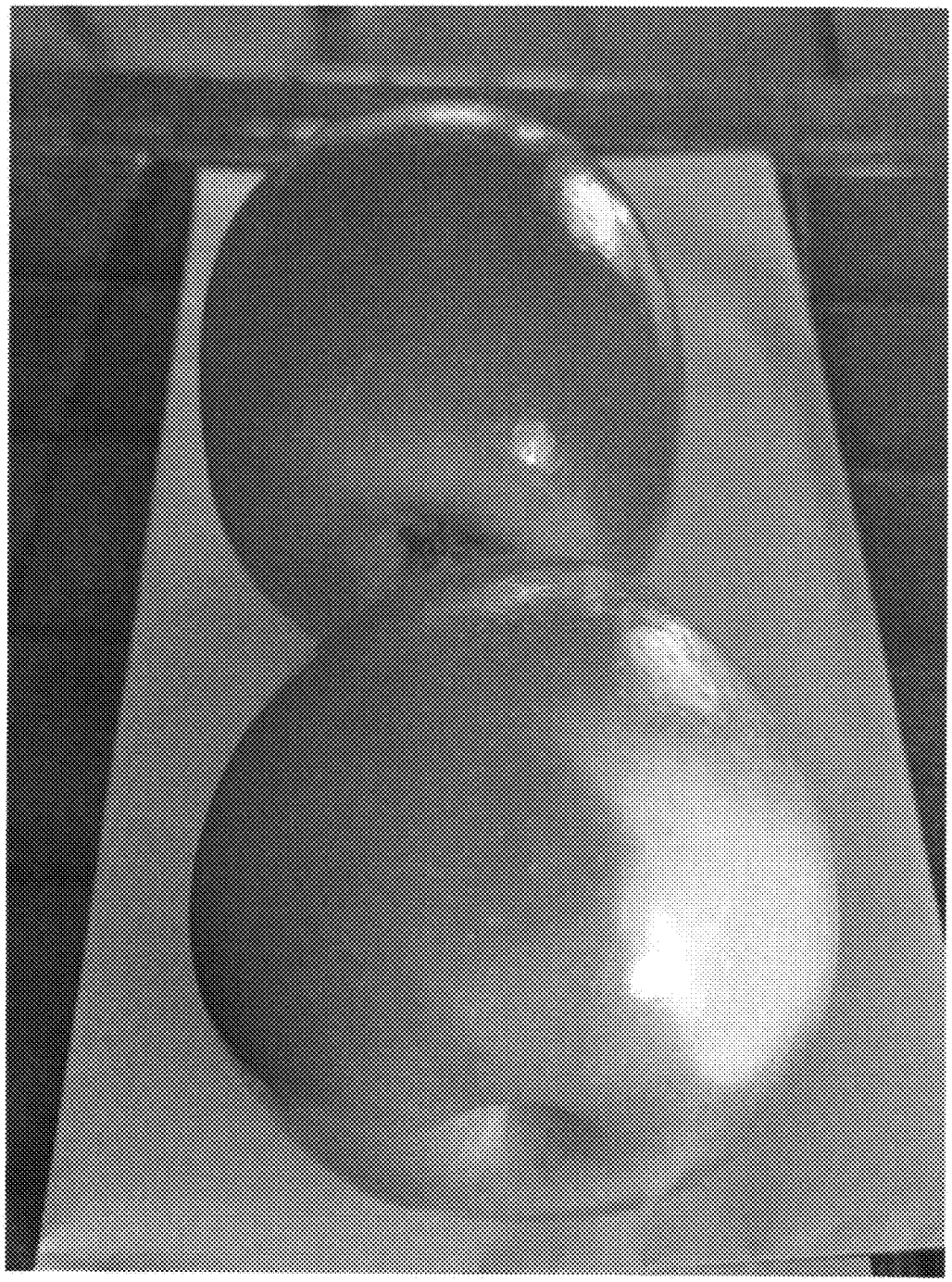
FIG. 5 shows mild cheddar background colour.
Figure 6:
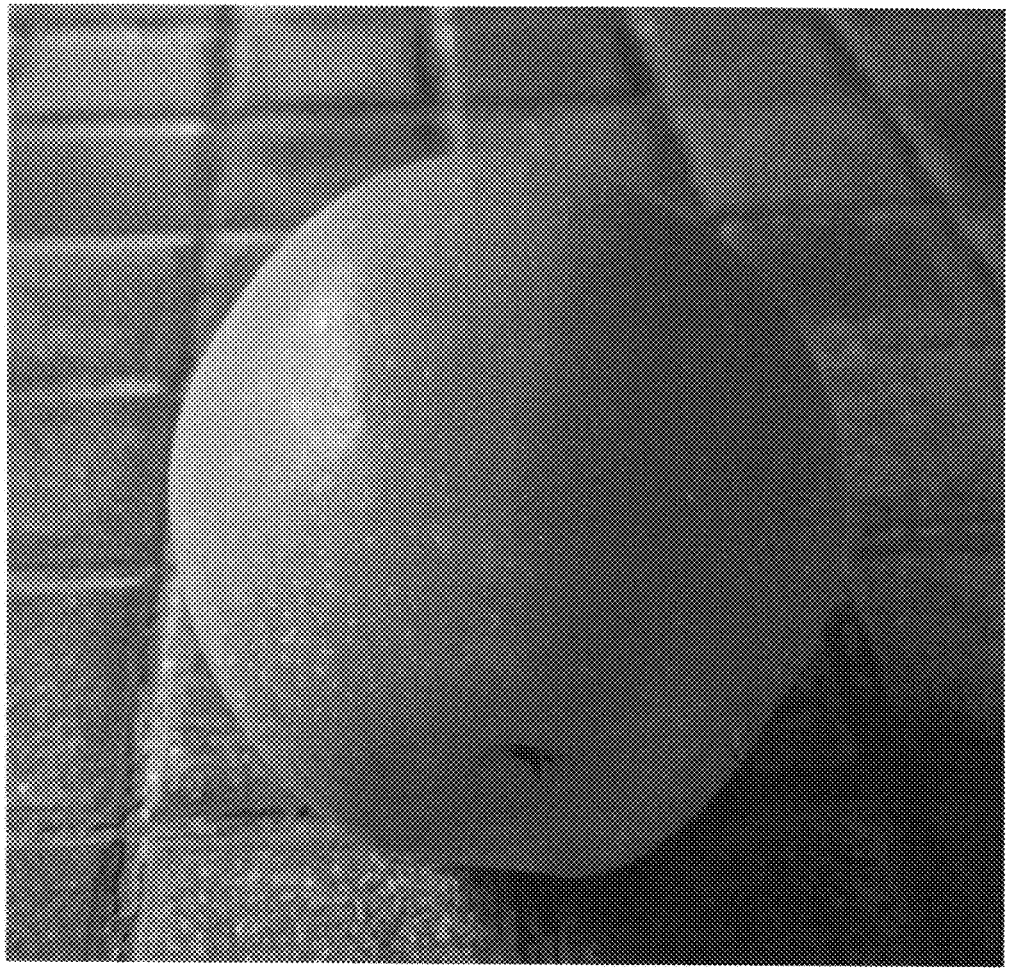
FIG. 6 shows vivid pink colouration extenuated by long periods of cool storage.
Figure 7:
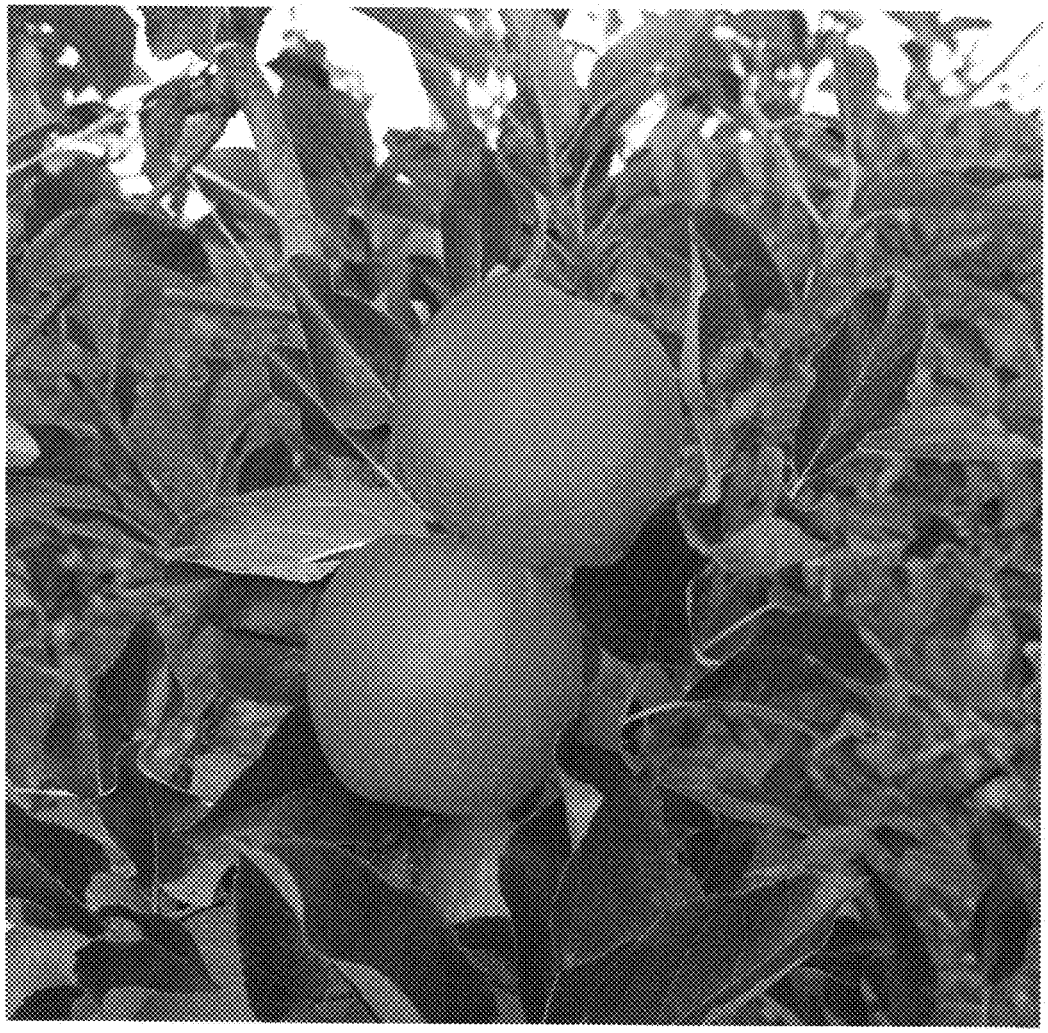
FIG. 7 shows the full colouration and maturity development of 'Seaton99' 10 days before 'Royal Gala' harvest.

The following is a detailed description of the new variety with colour terminology in accordance with The Royal Horticultural Society Colour Charts (R.H.S.C.C.). The new *Malus* variety 'Seaton99' has not been observed under all possible environmental conditions.

The aforementioned photographs together with the following observations and values, describe the trees of 'Seaton99' as grown in an orchard situated in Redwood Valley, Tasman District, Nelson Province of the South Island of New Zealand, Latitude S. 41, E2516661, N5989297, 36-50 m above sea level.

The planting site and climatic conditions closely approximate those generally used in commercial production of pipfruit, and the land areas in the vicinity have successfully been deployed in the production of pipfruit since the settlement of the Region, so that the location is generally viewed as a suitable site for commercial production.

The climate is in the temperate zone with summer temperatures generally below 30 deg C. and maximum 35 deg C. Winter temperatures range 7-16 deg C. with minimums minus 5-7 deg C.

The soil is variable and of modest fertility, being a mix of recent alluvial soils with clay type sub-soil, with fertility maintained by applications of fertiliser applied annually.

Trees are irrigated by drip irrigation when necessary. Annual rainfall is 900-1200 mm per year.

The trial blocks are substantially planted on CG 202 rootstock with the first commercial planting trial block now in $6^{th}$ year. Plantings are spaced 1.5 M between tree and 3.5 m row width giving a tree density of 2000 trees per hectare. All trees have performed identically in respect of fruit characteristics.

The type of bearing is early, being the first harvestable variety. Productivity is good with regular and heavy flowering and no bi-annual flowering evident.

Production on mature trees is estimated to be 20 kg-30 kg per tree.

Average size of mature trees is 3 m height and spread 1.4 m.

Trunk calliper is around 5 cm (10 cm above grafting).

Trunk texture is smooth with numerous lenticels slightly erased, approximately 3 lenticels per sq cm. Height=2 mm. Width=6 mm. Colour=dark grey RHS 198D.

Trunk bark colour brown-greyed RHS 197C and the lenticels are about 5 mm long×1.6 mm wide.

Branches number about 15 per tree and are angled generally 45-75 deg F. Natural growth tendencies have been suppressed by tying pendant as part of tree training management. Typical branch length is approximately 780 cm, with a diameter of approximately 19.5 cm. Texture is smooth. Interlode length=320 cm. Colour=grey, RHS 198A.

Leaves are evenly spaced along plant growth shoots. Leaf shape is conically elongated from a broader base to a sharp apex. The margin is tightly serrated. The front texture is waxy and the rear displays a "matte finish". Leaves have an even venation pattern with staggered joints on each side from the main rib. Front surface colour is medium green RHS 146A. Reverse surface colour is a pale green RHS 148A.

Petiole length=41 cm, with a diameter of 2 cm. Petiole colour is light brown RHS 152B.

Blooming time in Redwood Valley is from early October until the 3rd week of October with staggered later heavy flowering on one year old wood. The flowers are borne in clusters with approximately 6 flowers per cluster. Flowers can also be borne singly. The average flower depth is 15 mm and flower diameter is 35 mm.

The flower bud shape is bulbous, round with an average bud length of 13 mm and bud diameter of 9 mm. The flower bud colour is 134B. The average number of petals is 5, with an average petal length of 20 mm and petal width of 12 mm. The petals have an oval shape. The petal apex is rounded with no distinct point (*rotundifolus*). The petal margin is entire (*forma integra*). The abaxial petal texture is soft, smooth and lightly veined, while the adaxial petal texture is soft and veined. The abaxial and adaxial surfaces of the petal both have a colour of 62D.

The average number of sepals is 5, with an average sepal length of 9 mm and sepal width of 4 mm. The sepals have a triangular shape to a pointed tip. The sepal apex is sharp and pointed. The sepal margin is fringed by hairs (*ciliatus*). The abaxial sepal texture and the adaxial sepal texture are both heavily covered by hairs. The abaxial and adaxial surfaces of the sepal both have a colour of 134B.

Fruit maturity commences second week of February which is about 125 days after flowering.

The harvest window is from early- mid February until early March.

Keeping quality is good on the tree and in storage. In Coolstore at 0.5 deg C. trials with Smartfresh™ have stored good quality outcomes to 280 days. Shipping trials performed in 2017 indicate good storage and handling characteristics, with up to 200 days post-harvest on trials to date.

Fruits are conical-truncated with an average fruit height of 70 mm, fruit diameter of 77 mm, and weight around 240 gm.

Stem length is around 27 mm with a diameter of 2.7 mm. Colour of the stem is 21C.

Stem cavity depth is 10 mm with a width of 35 mm and has some smooth russet on about 40% of the fruits.

Stem cavity depth is 10 mm and has some smooth russet on about 40% of the fruits.

The typical observed eye basin width is 31 mm and eye basin depth is 16 mm. The crowning at the apex contains very slight crowns, and the sepals are positioned at the base of the petals. The calyx tube forms a cuplike funnel.

Skin is smooth texture of medium thickness.

Firmness at harvest time 7.8 kg-9.4 kg.

Colour is around RHS 52A with background lemon 1D and the random "flecking" characteristic 158B. The fruit pattern overcolour is bright pink/orange. Fruit flesh texture is crisp and juicy, with a sugar content of 12.2. The fruit flesh colour is 2C.

The fruit core is oblongated. Approximately 5 fruit locule per fruit, where the fruit locule form contains segregated interconnecting chambers. The average fruit locule length is 18 mm and average fruit locule width is 5 mm. Seeds per fruit is about 6 and per locule 1-2. The seeds are oblong and pear shaped with a smooth texture and a colour of 177A. Seed length is 7.7 mm-width 4.7 mm.

The typical number of pistils is 5 and the average pistil length is 13 mm. The average anther length is 2.5 mm with a colour of 1C. The average stigma length is 0.5 mm with a colour of 142B. The average style length is 8 mm with a colour of 142C. The average ovary length is 3 mm with a colour of 130A. The pollen amount is abundant and the pollen has a colour of 14A.

Propagation is from budding and grafting on GC202 (patented) rootstock.

Light intensities—full sunlight or slight shade. A small trial area using light-reflective cloth has been conducted with anticipated outcome of increased percentage of foreground colour. The trial area will be increased.

Pruning requirements are similar to heritage "GALA", requiring removal of strong upright growth, and systematic renewal of fruiting wood. The trees perform well with branches trained into a pendant position of approximately 45% below horizontal. Flower numbers are very high and require heavy blossom thinning over the bloom period.

Tree vigour is moderate with upright form and good ramification.

Main branches develop with flat angles around 45%-50% if not trained down.

Climatic hardiness appears normal tolerance for planted site which experiences summer temperatures in the mid to high 30's (Celsius) and winter temperatures down to −10 deg C.

Disease/pest susceptibility is evident to black spot (scab), and powdery mildew at increased incidence requiring dedicated control.

Climatic hardiness appears normal tolerance for planted site which experiences summer temperatures in the mid to high 30's and winter temperatures down to −10 deg C.

I claim:

1. A new and distinct apple tree named 'Seaton99' as illustrated and described herein.

* * * * *